(12) United States Patent
Tepic et al.

(10) Patent No.: US 11,406,423 B2
(45) Date of Patent: Aug. 9, 2022

(54) MODULAR EXTERNAL FIXATOR AND METHOD OF ITS USE

(71) Applicant: Kyon AG, Zürich (CH)

(72) Inventors: Slobodan Tepic, Zurich (CH); Stephen Bresina, Davos (CH)

(73) Assignee: Kyon AG, Zürich (CH)

( * ) Notice: Subject to any disclaimer, the term of this patent is extended or adjusted under 35 U.S.C. 154(b) by 244 days.

(21) Appl. No.: 16/603,081

(22) PCT Filed: Apr. 6, 2018

(86) PCT No.: PCT/EP2018/058843
§ 371 (c)(1),
(2) Date: Oct. 4, 2019

(87) PCT Pub. No.: WO2018/185275
PCT Pub. Date: Oct. 11, 2018

(65) Prior Publication Data
US 2021/0106358 A1    Apr. 15, 2021

(30) Foreign Application Priority Data

Apr. 7, 2017   (EP) ..................................... 17165580

(51) Int. Cl.
*A61B 17/64* (2006.01)
*A61B 17/84* (2006.01)

(52) U.S. Cl.
CPC ...... *A61B 17/6416* (2013.01); *A61B 17/6466* (2013.01); *A61B 17/846* (2013.01)

(58) Field of Classification Search
CPC ............ A61B 17/6416; A61B 17/6466; A61B 17/7053; A61B 17/823; A61B 17/82; A61B 17/842
See application file for complete search history.

(56) References Cited

U.S. PATENT DOCUMENTS

| | | | |
|---|---|---|---|
| 4,502,473 A * | 3/1985 | Harris | A61B 17/6491 606/58 |
| 5,454,810 A | 10/1995 | Pohl et al. | |
| 9,539,029 B1 | 1/2017 | Muniz et al. | |
| 2011/0082458 A1 | 4/2011 | Crozet et al. | |
| 2014/0276816 A1 | 9/2014 | Cresina et al. | |

FOREIGN PATENT DOCUMENTS

| | | |
|---|---|---|
| CN | 2643848 Y | 9/2004 |
| EP | 0431441 A1 | 6/1991 |
| JP | H04-300533 A | 10/1992 |
| JP | H08-502662 A | 3/1996 |
| JP | H09-215699 A | 8/1997 |

OTHER PUBLICATIONS

JP 1925-017060; Author/Inventor unknown. (Year: 1925).*

(Continued)

*Primary Examiner* — Julianna N Harvey
(74) *Attorney, Agent, or Firm* — Rothwell, Figg, Ernst & Manbeck, P.C.

(57) ABSTRACT

The invention relates to an external fixator device and a method of its use in treating bone fractures and in orthopedic interventions, such as corrective osteotomies.

19 Claims, 2 Drawing Sheets

(56) References Cited

OTHER PUBLICATIONS

Figure 1:
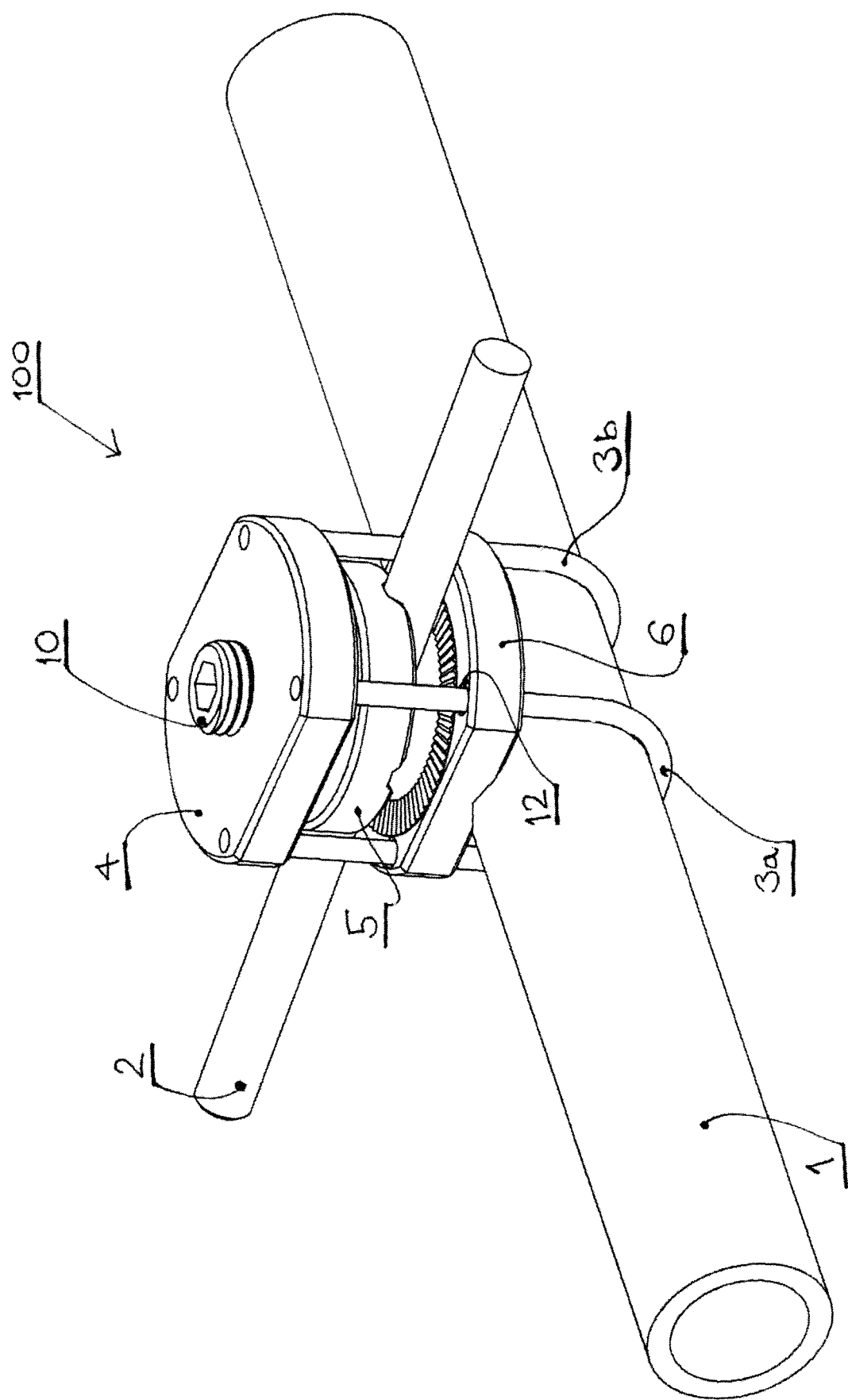

European Search Report cited in EP 17 16 5580 dated Feb. 2, 2018, 3 pages.
International Search Report cited in PCT/EP2018/058843 dated Jun. 28, 2018, 4 pages.
Notification of Reasons for Rejections issued in JP Patent Application No. 2019-540010 dated Feb. 10, 2022, 9 pages.
Chinese Office Action dated May 16, 2022 issued in Application No. 201880012280.4, 12 pages.

* cited by examiner

MODULAR EXTERNAL FIXATOR AND METHOD OF ITS USE

CROSS REFERENCE TO RELATED APPLICATION

This application is a continuation of PCT/EP2018/058843, filed Apr. 6, 2018, which claims the benefit of European Patent Application No. 17165580.6 filed on Apr. 7, 2017, the disclosures of which are incorporated herein in their entirety by reference.

FIELD OF THE INVENTION

The invention relates to an external fixator device and a method of its use in treating bone fractures and in orthopedic interventions, such as corrective osteotomies.

BACKGROUND

Fractured bones and corrective osteotomies are surgically treated by means of one of the three generic medical device families: (i) plates and screws; (ii) intramedullary nails, and (iii) external fixators. Selection of external fixation by trauma and orthopedic surgeons is greatly influenced by their background, attitude, place of practice and general economic conditions in addition to the nature of the medical problem to be treated. This greatly complicates any estimates of what the number of cases being treated by any of the methods might be worldwide, but all three are universally considered as fundamentally important surgical aids.

In many cases, internal fixation by plates or nails is simply not possible in most of the undeveloped world, thus making external fixation the only potentially viable, modern alternative to complement conservative treatments by fracture splinting or casting. Unfortunately, the costs of external fixators produced in the developed world are also prohibitive for most of the undeveloped countries.

The main drawback of external fixation is the rather uncertain and uneven progress of bone healing when compared to internal fixation. Passage of bone pins or wires through soft tissue surrounding the bone and the skin increases the risk of infection when the fixator is kept on the patient for a long period of time, e.g. several months.

Much of the uncertainty can be explained in view of rather recent research findings, which have elucidated different biological phases of fracture healing that call for different mechanical conditions at the fracture site. In the very early stages, in the first week or two, as the repair is initiated, differentiating factors emanating from the surrounding bone need to provide signals to the proliferating cells in the fracture zone to actually turn themselves into bone forming cells. In absence of any movement across the fracture, or the osteotomy, mass transport of the signals out of the bone and throughout the zone of repair is limited to diffusion, which may not suffice when the gaps of the fracture are in excess of some hundreds of micrometers. Formation of fibrous tissue in the gap, which is what tends to quickly fill any tissue defects, may slow down, if not totally frustrate formation of bone proper, leading to delayed unions or non unions. Movement, and particularly compression of the gap promotes convective mass transport of the biological factors out of the bone and within the gap, driving the differentiation process towards bone formation.

After this early period, however, once the early organic matrix for bone has been produced and the mineralization starts to set in, excessive movement will prevent bridging of the gaps between the nuclei of mineralization and disrupt the healing process. Thus, at this stage of the healing process, in order to facilitate a safe and thorough process of mineralization, the movement across the gap should be reduced as much as possible calling for as stiff a construct of the external fixator as possible.

In the final stages of fracture union, presence of the stiff external fixator, however, may hinder remodeling of healed bone by reducing the full physiological loading it will need to support once the fixator is removed, so again, a change in fixator stiffness, back to low, is called for.

There are numerous ways in which this modulation can be carried out with conventional external fixators, but most of them require tedious and complex measures. Thus, there is a need to provide an external fixator which overcomes the problems associated with the state of the art.

DESCRIPTION OF THE INVENTION

The present inventors have provided a novel fixator which is designed to allow insertion of bone pins in parallel fashion, but also at an oblique angle to each other. The stiffness of such a construct with no more than two bone pins parallel to each other is much higher than of that with all pins parallel.

Modulation of the overall stiffness can be effected by locking either only two, or all three of the pins inserted in a bone segment. For the maximum effect of modulation the external frame that holds the bone pins together needs to be as stiff as possible. It also needs to lock the pins very stably against the bending and axial forces.

The fixator of this invention fulfills the mechanical requirements outlined above, but it also solves the problem of production at costs affordable to even some of the undeveloped world. Its deployment in the developed world can reduce the overall costs of the medical treatment not only because of the lower price of the hardware, but because, and more importantly, if used according to the proposed method, it can shorten the time of healing process and avoid unnecessary further surgeries.

The invention discloses an external fixator clamp with a shape and function of a yoke, adapted to clamp a bone pin to a support element that bridges the distance from one to the other segment of the fractured bone. Clamps according to this invention require very small amount of materials for production of clamp components that are also of simple shapes and well suited for efficient manufacturing. The strength of the external fixator construct with 6 pins and 6 clamps has been demonstrated to match or exceed that of a double rod conventional frame using 12 clamps for 6 pins.

The clamp and an external fixator comprising said clamp can be used in human and veterinary medicine.

In one aspect, an external fixator according to the present invention comprises:
(i) at least one external support element (1),
(ii) a plurality of bone pins (2),
(iii) at least one fixing element (100) for fixing a bone pin to the support element, and
(iv) optionally at least one connecting element to connect several external support elements to each other.

A further aspect of the present invention is directed to a method for external fixation of a bone, comprising applying the fixator to a subject in need thereof. The method is particularly suitable for the treatment of bone fractures and in orthopedic interventions, such as corrective osteotomies.

The external support element may be a tube or a solid rod. It may have a straight or curved shape depending on the mechanical requirements of the fracture to be fixed. The device may comprise one or more external support elements. If several support elements are present, they may be connected to each other by connecting elements such as clamps or bars.

The bone pins are designed to be inserted on one side into the bone to be fixed. Usually, at least three bone pins are used per bone segment, i.e. on either side of the fracture to be fixed.

The stiffness of the construct may be modulated by using a fixing element, in the following designated as a clamp, which can be tightened or loosened depending on the stage of the bone healing process.

In the device of the present invention, each bone pin may be fixed to a single support element at a single fixing point. The bone pins can be placed either perpendicularly to the support element or at an oblique angle to the support element. They may be inserted through fixing elements aiming at the bone from either side of the support element (in the following, this element of the fixator is designated as "tube", but it is clear that a "solid rod" may serve the same function). The diameter of the tube is usually on the scale of cross sectional dimensions of the bone being treated, thus fixing the pins to opposite sides of the tube, gives the construct an added three dimensional stability.

In a preferred construct two bone pins are inserted parallel to each other and perpendicular to the tube on each side of the fracture. More preferably, these bone pins are fixed to opposite sides of the tube. Further, third bone pins are inserted into the bone at an oblique angle to the other pins and to the tube on each side of the fracture.

At the time of surgery, the third bone pin is not clamped tight to the tube. Selectively clamping the bone pins allows for modulation of the construct stiffness. In this preferred configuration, with two parallel bone pins perpendicular to the frame and one oblique bone pin per bone segment, locking the oblique bone pin in addition to the perpendicular bone pins will increase the overall stiffness of the device 2 to 3 times, depending on the tube intrinsic stiffness. This factor of modulation also depends on the stiffness of the bone pins and the bone itself, but it is invariably much higher than what can be achieved by, for example, additionally locking the third bone pin in a more conventional configuration with all three bone pins being parallel to each other, which brings only a fractional increase in construct stiffness.

Properly modulating the construct stiffness between biologically distinct phases of bone healing can dramatically reduce the time of healing and improve the strength of the healed defect. Particularly, and in contrast to the well-accepted notion of dynamization promoted by the company Orthofix in the context of external fixation, an initial period of one to two weeks with low stiffness, followed by an increased stiffness of the construct, leads to an outcome superior to what can be obtained by keeping either low or high stiffness throughout the healing process, or to switching from initially high to low stiffness (J Bone Joint Surg Am. 2012 Nov. 21; 94(22):2063-73. doi: 10.2106/JBJS.K.01604. Improved healing of large segmental defects in the rat femur by reverse dynamization in the presence of bone morphogenetic protein-2. Glatt V, Miller M, Ivkovic A, Liu F, Parry N, Griffin D, Vrahas M, Evans C).

In this context, the term "reverse dynamization" is used to describe stepping up from low to high stiffness of the external fixator construct during the course of the healing process. Correspondingly, the term "dynamization" is used to describe stepping down from high to low stiffness. According to the present invention, a dynamization of the construct may be deployed towards the end of the treatment, not at the start. Changing the stiffness of the construct according to the present invention is a simple, ambulatory intervention—the clamps holding one of the bone pins on each side of the fracture that were not fixed tight at the time of surgery are now clamped tight.

In the following, preferred embodiments of the invention are described in reference to the accompanying Figures.

FIG. 1 shows a perspective view of the external fixator clamp 100 according to the present invention showing a segment of the tube 1 and a bone pin 2 clamped together with the clamp.

Figure 2:
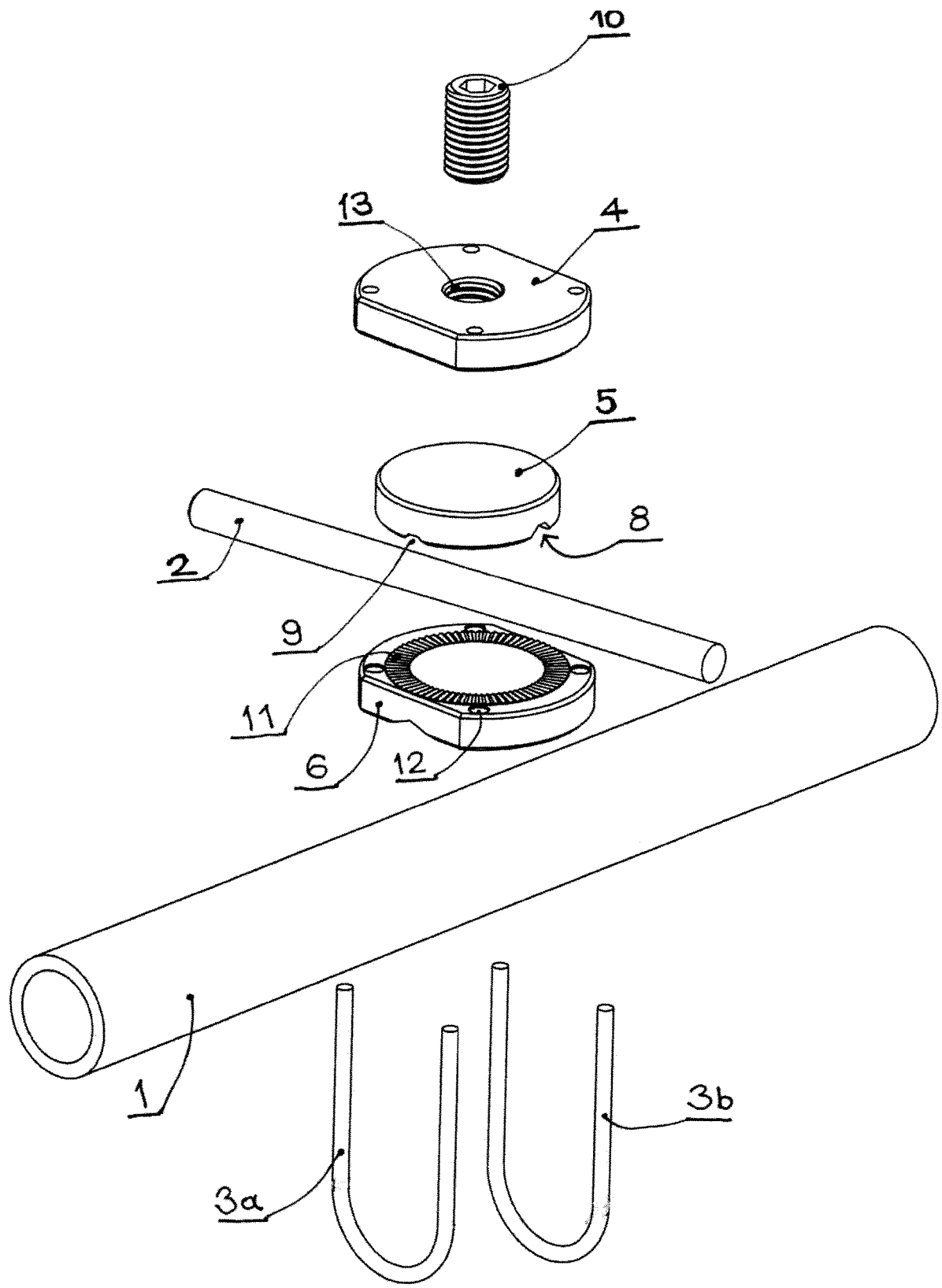

FIG. 2 shows an exploded view of the components of the external fixator.

The clamp 100, FIG. 1, of the present invention is made from mechanically rather simple elements shown separately on FIG. 2:

(1) two wire elements 3a and 3b, e.g. flexible wire elements, bent to fit around the tube 1 and connected, preferably by welding, to a top plate 4 with a threaded hole 13 in the center, resulting in a yoke shaped member;

(2) an additional bottom plate 6 in contact with the tube which may have holes, e.g. four holes 12 for passage of the bent wires of the yoke and a transverse recess 7 on one face to fit over the tube and make two lines of contact with it—in the following also designated as tube plate;

(3) a disc 5 that fits between the top plate 4 of the yoke and the tube plate 6, within the wires 3 of the yoke, with transverse recesses 8, 9 adapted to different bone pin diameters—in the following also designated as pin disc;

(4) a set screw 10 in the top plate of the yoke, tightening of which will compress the pin disc 5, the bone pin 2, the tube plate 6 and the tube 1, all at once, within the yoke 100.

A clamp comprising the elements as described above allows a very stable clamping of the bone pin to the tube. On the upper surface of the tube plate, facing the pin, a ring 11 of small teeth, or otherwise roughened surface, provides even a stronger grip on the pin to prevent its rotation or sliding against the tube plate 6. Before the clamping is effected by tightening of the set screw, the bone pin and the tube have 5 degrees of freedom of relative movement. Thus, the stiffness of the construct can be modulated by tightening and loosening of the set screw allowing dynamization or reverse dynamization as indicated above.

Production costs of such a clamp are much lower than of the conventional external fixator clamps and thus should be affordable in undeveloped world, where currently only conservative treatments by splinting or casting are viable options of fracture treatment.

In much of the developed world the unpredictable outcomes of conventional external fixation in comparison to plating or nailing have reduced its use to only temporary stabilization of the open fractures, followed by internal fixation. However, if the external fixation by reverse dynamization finds it way from research into clinical practice, reliable and fast healing by external fixation could significantly reduce the cost and the morbidity of multiple interventions currently practiced.

FIG. 1 shows a perspective view of the external fixator clamp according to the present invention. The clamp 100 is comprised of two identical, U-shaped wires 3a and 3b fixed to the top plate 4 of the clamp. Fixation of the wires 3a and 3b into the top plate 4 can be accomplished by means of welding, hard soldering, brazing or riveting, particularly orbital riveting. This construct has a mechanical function of a yoke. A bottom plate 6 contacting the support element 1 is provided with four through-holes 12 and is free to slide along the wires 3a and 3b. The bottom plate 6 on its support element-facing side may have a transverse groove 7 that provides improved contact to the support element 1, for example along two parallel lines if trapezoidally shaped. A bone pin 2 is placed between the pin disc 5 and the bottom plate 6. On its bone pin facing side the pin disc 5 may have one or more transverse recesses 8, 9, which accommodate bone pins of different diameters.

FIG. 2 shows an exploded view of the tube, pin and the clamp parts. The clamp components 3a, 3b, 4, 5, 6 and 10 may be manufactured from a suitable metal, such as a stainless steel, a titanium alloy or a high strength aluminium alloy. Titanium or aluminium alloys are preferred to stainless steels because they are compatible with MRI, which can be used to assess the progress of fracture healing. The tube 1 has sufficient strength when made from aluminium alloys such as 7075 and of large diameter.

Mechanical testing of the external fixator according to this invention with one large diameter tube and 6 clamps, has been performed to compare it to a conventional, Hoffman-type fixator with two rods and six pins clamped to the rods with 12 clamps. The strength and the stiffness exceeded the values of the conventional construct.

Of some importance is also the reduced weight of the complete frame, even if stainless steel is used; use of titanium or aluminum alloys brings an additional weight reduction of factor two to four. While this is of only minor clinical importance, reduced weight has direct impact on the manufacturing costs.

The key contributing factor and inventive technical aspect of the solution to weight and cost reduction is the use of two thin wires 3a and 3b to form the yoke structure of the clamp, which can effectively sustain the tensile loads imposed by compressing the pin 2 to the tube 1 via tube plate 6 by tightening of the set screw 10.

The invention claimed is:

1. A device for external fixation of at least one bone, the device comprising:
   (i) at least one external support element;
   (ii) a plurality of bone pins; and
   (iii) at least one fixing element for fixing a bone pin to the at least one external support element, wherein
   the at least one fixing element comprises a top plate, a bottom plate, and a plurality of wire elements,
   the top plate and the bottom plate are spaced apart to receive a bone pin between the top plate and the bottom plate,
   the bottom plate is in contact with the at least one external support element, and
   the plurality of wire elements slidingly pass through the bottom plate, are fixed into the top plate and are adapted to fit around the at least one external support element.

2. The device of claim 1, wherein
   the at least one fixing element is adapted to allow a stiffness modulation,
   a low degree of stiffness is adjusted during a first phase of the healing period, and
   a higher degree of stiffness is adjusted during a subsequent phase of the healing period.

3. The device of claim 1, wherein the at least one fixing element is shaped as a clamp around the bone pin and the at least one external support element.

4. The device of claim 1, wherein the at least one fixing element further comprises a pin disc between the top plate and the bottom plate for receiving the bone pin between the pin disc and the bottom plate.

5. The device of claim 4, wherein the exterior circumference of the pin disc is within the plurality of wire elements.

6. The device of claim 4, wherein the bottom plate has a roughened surface on the side facing the bone pin.

7. The device of claim 4, wherein the pin disc has one or more transverse recesses on the side facing the bone pin.

8. The device of claim 1, wherein the bottom plate has a transverse recess on the side facing the support element.

9. The device of claim 1, wherein the top plate comprises an adjusting element which is adapted to allow a stiffness modulation.

10. The device of claim 9, wherein the adjusting element is a set screw.

11. The device of claim 1, comprising at least three bone pins for insertion into the at least one bone on each side of a fracture of the at least one bone to be fixed, wherein
   the at least three bone pins comprise a first bone pin, a second bone pin, and a third bone pin, and
   the first and second bone pins are adapted for insertion parallel to each other and the third bone pin is adapted for insertion at an oblique angle to the first and second bone pins.

12. The device of claim 11, wherein the first and second bone pins are for fixation to opposite sides of the at least one external support element.

13. The device of claim 11, wherein the first and second bone pins are for fixation perpendicular to the at least one external support element.

14. The device of claim 11, wherein
   said at least one fixing element comprises an adjusting element, and
   a degree of the stiffness of the device is adjustable by using the adjusting element.

15. The device of claim 14, wherein
   the degree of the stiffness of the device is a first degree when said adjusting element is located at a first position, and
   the degree of the stiffness of the device is a second degree when said adjusting element is located at a second position.

16. The device of claim 1, further comprising at least one connecting element to connect several external support elements to each other.

17. A method for external fixation of at least one bone, comprising applying a device to the at least one bone, wherein the device comprises:
   (i) at least one external support element;
   (ii) a plurality of bone pins; and
   (iii) at least one fixing element for fixing a bone pin to the at least one external support element, wherein
   the at least one fixing element comprises a top plate, a bottom plate, and a plurality of wire elements,
   the top plate and the bottom plate are spaced part to receive a bone pin between them,
   the bottom plate is in contact with the at least one external support element, and
   the plurality of wire elements are fixed into the top plate, slidingly pass through the bottom plate and are adapted to fit around the at least one external support element.

18. The method of claim 17, comprising modulating the stiffness of the device during the healing period, wherein
   a low degree of stiffness is adjusted during a first phase of the healing period, and a higher degree of stiffness is adjusted during a subsequent phase of the healing period.

19. The method of claim 18, further comprising a low degree of stiffness is adjusted during the final phase of the healing period.

* * * * *